(12) United States Patent
Amar

(10) Patent No.: US 11,767,283 B2
(45) Date of Patent: Sep. 26, 2023

(54) ANTI-INFLAMMATORY COMPOUNDS

(71) Applicant: Salomon Amar, Teaneck, NJ (US)

(72) Inventor: Salomon Amar, Teaneck, NJ (US)

(*) Notice: Subject to any disclaimer, the term of this patent is extended or adjusted under 35 U.S.C. 154(b) by 0 days.

(21) Appl. No.: 16/502,284

(22) Filed: Jul. 3, 2019

(65) Prior Publication Data
US 2020/0010396 A1    Jan. 9, 2020

Related U.S. Application Data

(60) Provisional application No. 62/694,265, filed on Jul. 5, 2018.

(51) Int. Cl.
| | | |
|---|---|---|
| *C07C 49/563* | (2006.01) | |
| *A61P 29/00* | (2006.01) | |
| *A61P 1/02* | (2006.01) | |
| *A61P 19/02* | (2006.01) | |

(52) U.S. Cl.
CPC .............. *C07C 49/563* (2013.01); *A61P 1/02* (2018.01); *A61P 19/02* (2018.01); *A61P 29/00* (2018.01)

(58) Field of Classification Search
CPC .................................................. C07C 49/563
See application file for complete search history.

(56) References Cited

PUBLICATIONS

Cai et al. Bioorg. Med. Chem. Lett. 2018, 28, 2667-2669 (Year: 2018).*
Ouertatani-Sakouhl et al. J. Biol. Chem. 2010, 285, 26581-26598 (Year: 2010).*
Vovk et al. Russian Journal of Organic Chemistry 2004, 40, 280-281 (Year: 2004).*
National Center for Biotechnology Information. PubChem Database. Source=PCMD, AID=846, https://pubchem.ncbi.nlm.nih.gov/bioassay/846 (deposit date Nov. 15, 2008, accessed on Sep. 24, 2019) (Year: 2008).*
National Center for Biotechnology Information. PubChem Database. CID=1474654, https://pubchem.ncbi.nlm.nih.gov/compound/1474654 (created on Jul. 11, 2005, accessed on Sep. 24, 2019) (Year: 2005).*
Kim et al. Arch Pharm Res 2003, 26, 192-196 (Year: 2003).*
Khlebnikova et al. Russian Journal of General Chemistry 2007, 77, 1724-1731 (Year: 2007).*
Foster et al. Bioorg. Med. Chem. 1999, 7 2415-2425 (Year: 1999).*
The Jackson Laboratory Handbook of Genetically Standardized Mice, 2009, pp. 1-380 (Year: 2009).*
Shimizu, S. The Laboratory Mouse, Routes of Administration 2004, Chapter 32, pp. 527-541 (Year: 2004).*
Alshammari et al. J. Clin. Periodontol. 2017, 44, 1123-1132 (Year: 2017).*
Alshammari et al., "Kava-241 Reduced Periodontal Destruction in a Collagen Antibody Primed Porphyromonas gingivalis Model of Periodontitis," J Clin Periodontol, Nov. 2017, vol. 44, No. 11; pp. 1123-1132.
Huck et al., "Identification of a Kavain Analog with Efficient Anti-inflammatory Effects," Scientific Reports, Nature Research, Sep. 10, 2019, vol. 9, 12950; pp. 1-10.

* cited by examiner

*Primary Examiner* — Matthew P Coughlin
(74) *Attorney, Agent, or Firm* — Carter, DeLuca & Farrell LLP; George Likourezos

(57) ABSTRACT

Synthetic kava analog compounds of formula I are disclosed. Specifically, kava analogs of the structural type 3-oxoclclohex-1-en-1-yl benzoates, and corresponding benzamides are disclosed. The compounds of the within invention are useful in the inhibition of cytokine TNF-α, the management of chronic inflammation such as but not limited to *Porphyromonas gingivalis* induced periodontitis, and in infective arthritis, either as compounds, pharmaceutically acceptable salts (when appropriate), pharmaceutical composition ingredients, whether or not in combination with other anti-inflammatory active pharmaceutical ingredients. Methods of treating chronic inflammation such as periodontitis and infective arthritis are also disclosed.

2 Claims, No Drawings

ANTI-INFLAMMATORY COMPOUNDS

This application claims priority from U.S. provisional application No. 62/694,265 filed Jul. 5, 2018.

FIELD OF THE INVENTION

The present invention relates to synthetic kava analog compounds of formula I having the structural type 3-oxo-clclohex-1-en-1-yl benzoates, and corresponding benzamides are disclosed. Specifically, the compounds of the within invention are useful in the inhibition of cytokine TNF-α, the management of inflammation such as periodontitis or in infective or rheumatoid arthritis, either as compounds, pharmaceutically acceptable salts (when appropriate), pharmaceutical composition ingredients, whether or not in combination with other anti-inflammatory active pharmaceutical ingredients. Methods of treating inflammation, periodontitis, infective arthritis and rheumatoid arthritis are also disclosed.

BACKGROUND OF THE INVENTION

Rheumatoid arthritis (RA) is a systemic autoimmune disease that causes chronic inflammatory responses of the capsule around the joints and the development of fibrous tissue in the synovium. The development of the pathology leads to the destruction of articular cartilage that is a consequence of sustained secretion of cytokines and cellular activation, especially of synovial macrophages. RA manifests by signs of inflammation with the affected joints being swollen, painful, warm and stiff. However, risk factors, cellular and molecular mechanisms involved remain under investigation with specific emphasis on the role of infectious pathogens. Interestingly, a role for periodontitis (PD) in aggravation of RA has been proposed, both diseases sharing some common features. PD is a chronic inflammatory disease of bacterial origin affecting tooth-supporting tissues, which can be triggered by multiple bacteria, including *Treponema denticola* and *Bactericides forsythus*. Progressive destruction of alveolar bone leads ultimately to tooth loss with consequences on masticatory function, quality of life and general health.

Several studies described the association between PD and systemic chronic diseases such as cardiovascular diseases, diabetes and RA. Recently, in a nationwide, population-based study in Taiwan, the risk of RA was higher in PD affected patients (Hazard ratio:1.89, CI:1.56-2.29). Interestingly, some interventional trials concluded that non-surgical treatment of PD lead to improvements of markers of activity in RA patients emphasizing the plausibility of the association between both diseases.

In this context, special attention has been placed on the role of infectious agents given that antibiotics had a beneficial effect in the management of certain cases of RA and strategies to alter microbiome or induced immune activation are suggested for the treatment of RA. More specifically, *Porphyromonas gingivalis*, a gram negative anaerobic bacterium and a purported periodontal pathogen, was proposed to play a key role in RA. Its detrimental effect was also confirmed in vivo in several mouse models where *P. gingivalis* infection exacerbated collagen antibody (AB) induced arthritis through different mechanisms including modification of gut microbiota and associated auto-immune response, neutrophils activation or induction of bone destruction.

Control of inflammation is a key element of RA treatment and, several drugs targeting cytokines such as TNF-α or IL-6 are currently being used. However, side effects such as parenteral delivery, immune suppression and high-cost warrant for alternatives. Kavain, a compound extracted from the *Piper methysticum* plant, has been credited for its antiarthritic and anti-inflammatory properties. Due to Kavain's potential toxicity, optimized kava analog compounds have been developed with results regarding prevention or management of inflammation.

The present invention is directed to novel synthetic kava analogs, and particularly Kava-241 that has demonstrated reduced TNF-α secretion in *Escherichia coli* LPS-stimulated RAW cells but has also prevented any inflammation including alveolar bone loss and associated with *P. gingivalis* induced PD in a collagen antibody primed mouse model. See Amar S., et al., *Kava-241 Reduced Periodontal Destruction in a Collagen Antibody Primed Porphyromonas gingivalis Model of Periodontitis*, J. Clin. Periodontol 44:1123-1132 (Jul. 26, 2017).

In addition, a recent study has identified Kava-205Me, a methylated kavain analog (5,5-dimethyl-3-oxocyclohex-1-en-1-yl 4-methylbenzoate), as demonstrating enhanced anti-inflammatory properties. See Amar, Salomon et al., *Identification of a Kavain Analog with Efficient Anti-inflammatory Effects*, [Currently unpublished], 2019. (Incorporated by reference in its entirety, herein). Specifically, in an in vitro assay of anti-inflammatory effects, murine macrophages (BMM) and THP-1 cells were infected with *P. gingivalis* (MOI=20:1) and a panel of cytokines were measured. Both cell types treated with Kava-205Me (10 to 200 µg/ml) showed significantly and dose-dependently reduced TNF-α secretion induced by *P. gingivalis*. In BMM, Kava-205Me also reduced secretion of other cytokines involved in the early phase of inflammation, including IL-12, eotaxin, RANTES, IL-10 and interferon-γ (p<0.05). In vivo, in an acute model of *P. gingivalis*-induced calvarial destruction, administration of Kava-205Me significantly improved the rate of healing associated with reduced soft tissue inflammation and osteoclast activation. In an infective arthritis murine model induced by injection of collagen-antibody (ArthriomAb)+*P. gingivalis*, administration of Kava-205Me was able to reduce efficiently paw swelling and joint destruction.

Therefore, the object of this invention is to provide synthetic kava analogs, such as Kava-241 and Kava-205Me, due to their anti-inflammatory effect and reduction in TNF-α secretion, to manage and/or treat chronic inflammatory diseases such as arthritis and joint inflammation in RA and inflammation in related PD.

BRIEF DESCRIPTION OF THE INVENTION

Synthetic kava analog compounds of formula I, as herein defined, are disclosed. These compounds, kava analogs of the structural type 3-oxoclclohex-1-en-1-yl benzoates, and corresponding benzamides, are useful in the inhibition of cytokine TNF-α, the management of inflammation in chronic diseases such as but not limited to *Porphyromonas gingivalis* induced periodontitis, and in infective arthritis and rheumatoid arthritis, either as compounds, pharmaceutically acceptable salts (when appropriate), pharmaceutical composition ingredients, whether or not in combination with other anti-inflammatory active pharmaceutical ingredients. Methods of treating chronic inflammation such as periodontitis and infective or rheumatoid arthritis are also disclosed.

DETAILED DESCRIPTION OF THE INVENTION AND PREFERRED EMBODIMENTS

The present invention is concerned with compounds of formula I, combinations thereof, or pharmaceutically acceptable salts thereof, in the inhibition, of cytokine TNF-α, the management of chronic inflammation such as but not limited to *Porphyromonas gingivalis* induced periodontitis and infective arthritis, and in the treatment of inflammation, periodontitis and infective and rheumatoid arthritis. Compounds of formula I are defined as follows:
1. A compound of the formula:

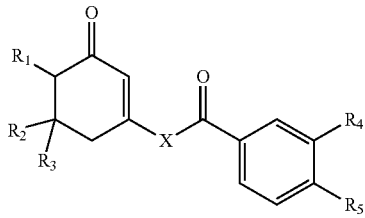

I wherein:
X is O or NH;
$R_1$ is H or ethoxycarbonyl;
$R_2$ and $R_3$ are H or $CH_3$; and
$R_4$ and $R_5$ are H, $CH_3$, Cl, F, methoxy, ethoxy or benzyloxy, or a pharmaceutically acceptable salt thereof.

This invention also encompasses a pharmaceutical composition useful for inhibiting cytokine TNF-α useful for managing or treating inflammation. Preferred compounds include compounds 1-16 of Table 1, below, in no particular order of preference. Most preferred to date is Compound 7, I-BC-241, BMCL 14 however further ongoing studies may conclude that additional compounds are equally or more effective.

TABLE 1

| Entry | Compound Name | Structure | Chemical Name |
|---|---|---|---|
| 1 | I-BC-205(Methyl) | 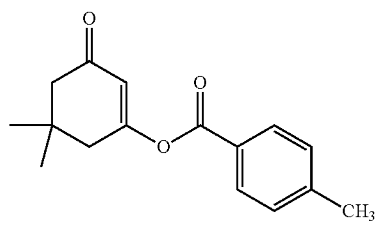 | 5,5-dimethyl-3-oxocyclohex-1-en-1-yl 4-methylbenzoate |
| 2 | I-BC-205(Cl) | 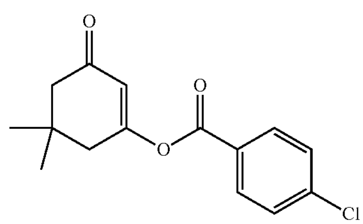 [SMILES: CC1(C)CC(=O)C=C(OC(=O)c2ccc(Cl)cc2)C1] | 5,5-dimethyl-3-oxocyclohex-1-en-1-yl 4-chlorobenzoate |
| 3 | I-BC-212 | 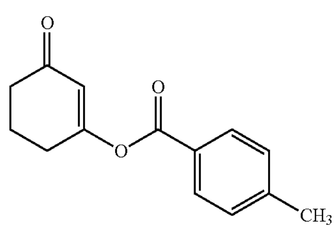 [SMILES: Cc1ccc(C(=O)OC2=CC(=O)CCC2)cc1] | 3-oxocyclohex-1-en-1-yl 4-methylbenzoate |
| 4 | I-BC-224 | 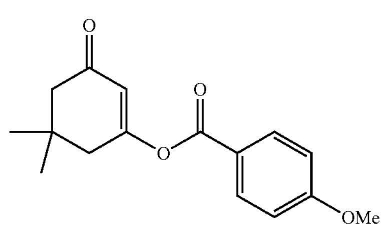 [SMILES: COc1ccc(C(=O)OC2=CC(=O)CC(C)(C)C2)cc1] | 5,5-dimethyl-3-oxocyclohex-1-en-1-yl 4-methoxybenzoate |
| 5 | I-BC-225 | 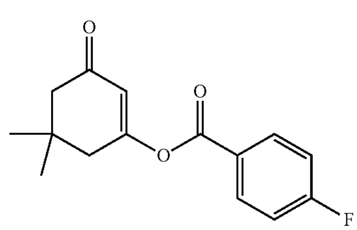 [SMILES: CC1(C)CC(=O)C=C(OC(=O)c2ccc(F)cc2)C1] | 5,5-dimethyl-3-oxocyclohex-1-en-1-yl 4-fluorobenzoate |

TABLE 1-continued

| Entry | Compound Name | Structure | Chemical Name |
|---|---|---|---|
| 6 | I-BC-240<br>BMCL 13 | 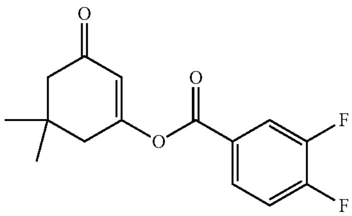 [SMILES: CC1(C)CC(=O)C=C(OC(=O)c2ccc(F)c(F)c2)C1] | 5,5-dimethyl-3-oxocyclohex-1-en-1-yl 3,4-difluorobenzoate |
| 7 | I-BC-241<br>BMCL 14 | 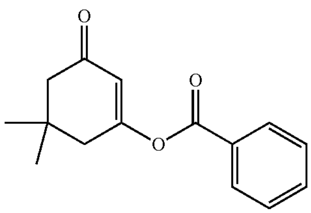 [SMILES: CC1(C)CC(=O)C=C(OC(=O)c2ccccc2)C1] | 5,5-dimethyl-3-oxocyclohex-1-en-1-yl benzoate |
| 8 | II-BC-006 | 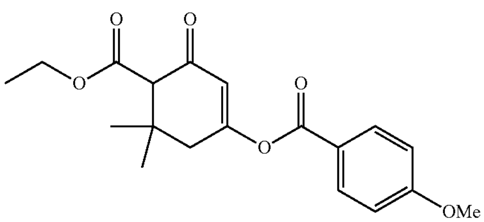 [SMILES: CCOC(=O)C1C(=O)C=C(OC(=O)c2ccc(OC)cc2)CC1(C)C] | 4-(ethoxycarbonyl)-515-dimethyl-3-oxocyclohex-1-en-1-yl 4-methoxybenzoate |
| 9 | II-BC-016<br>BMCL 15 | 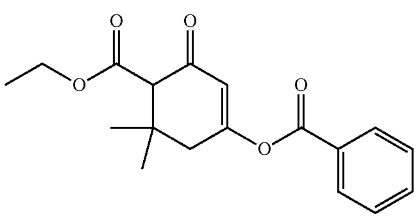 [SMILES: CCOC(=O)C1C(=O)C=C(OC(=O)c2ccccc2)CC1(C)C] | 4-(ethoxycarbonyl)-5,5-dimethyl-3-oxocyclohex-1-en-1-yl benzoate |
| 10 | II-BC-043 | 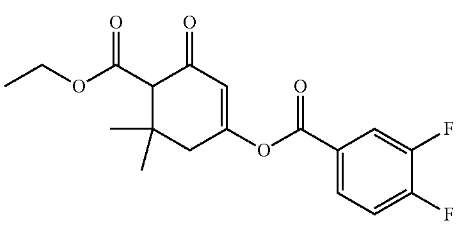 [SMILES: CCOC(=O)C1C(=O)C=C(OC(=O)c2ccc(F)c(F)c2)CC1(C)C] | 4-(ethoxycarbonyl)-5,5-dimethyl-3-oxocyclohex-1-en-1-yl 3,4-difluorobenzoate |
| 11 | III-BC-274 | 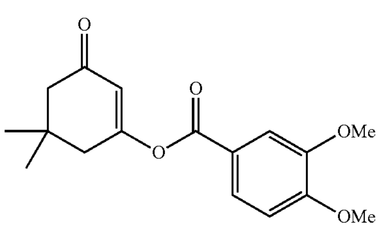 [SMILES: COc1ccc(C(=O)OC2=CC(=O)CC(C)(C)C2)cc1OC] | 5,5-dfmethyl-3-oxocyclohex-1-en-1-yl 3,4-dimethoxybenzoate |
| 12 | III-BC-284 | 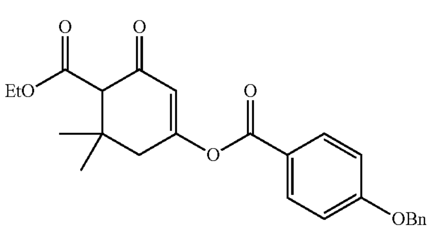 [SMILES: CCOC(=O)C1C(=O)C=C(OC(=O)c2ccc(OCc3ccccc3)cc2)CC1(C)C] | 4-(ethoxycarbonyl)-5,5-dimethyl-3-oxocyclohex-1-en-1-yl 4-(benzyloxy)benzoate |

TABLE 1-continued

| Entry | Compound Name | Structure | Chemical Name |
|---|---|---|---|
| 13 | III-BC-304 | 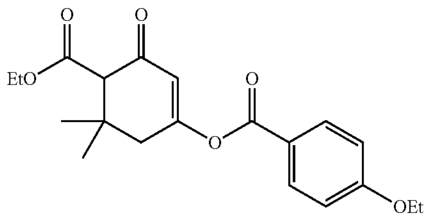 [SMILES: CCOC(=O)C1C(=O)C=C(OC(=O)c2ccc(OCC)cc2)CC1(C)C] | 4-(ethoxycarbonyl)-5,5-dimethyl-3-oxocyclohex-1-en-1-yl 4-ethoxybenzoate |
| 14 | VI-BC-227 BMCL 17 | 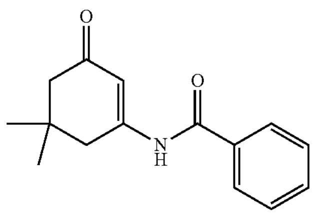 [SMILES: CC1(C)CC(=O)C=C(NC(=O)c2ccccc2)C1] | N-(5,5-dimethyl-3-oxocyclohex-1-en-1-yl) benzamide |
| 15 | VI-BC-228 BMCL 18 | 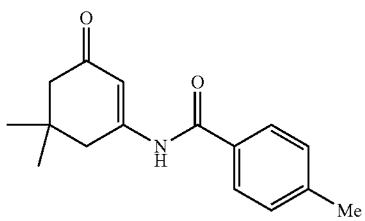 [SMILES: Cc1ccc(C(=O)NC2=CC(=O)CC(C)(C)C2)cc1] | N-(5,5-dimethyl-3-oxocyclohex-1-en-1-yl)-4-methylbenzamide |
| 16 | VI-BC-229 BMCL 19 | 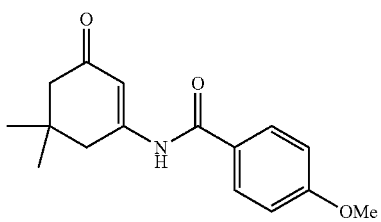 | N-(5,5-dimethyl-3-oxocyclohex-1-en-1-yl)-4-methoxybenzamide |

The compounds of the present invention can be synthesized by the following methods. The synthetic approach towards cyclohexanone benzoates (entries 1-7 and 11) is based on the O-acylation of the highly enolizable cyclic 1,3-diketones. Accordingly, treatment of 1,2-dichloroethane solution of commercially available 1,3-cyclohexanedione with various benzoyl chlorides in the presence of pyridine efficiently provided the O-acylated enol derivatives. They were further transformed to β-ketoesters through the C-acylation of in situ generated lithium enolate using Mander's reagent (ethyl cyanoformate). Thus, cyclohexanone benzoates were treated with lithium bis(trimethylsilyl)amide solution (LHMDS) to generate lithium enolates. The subsequent nucleophilic attack (C-acylation) of the enolate with ethyl cyanoformate was facilitated by additive 1,3-Dimethyl-3,4,5,6-tetrahydro-2(1H)-pyrimidinone (DMPU), cleanly providing β-ketoesters (entries 8-10 and 12-13) without trace of O-acylation products, in accordance with the following scheme:

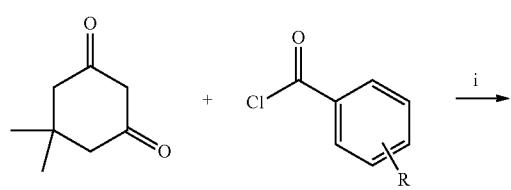

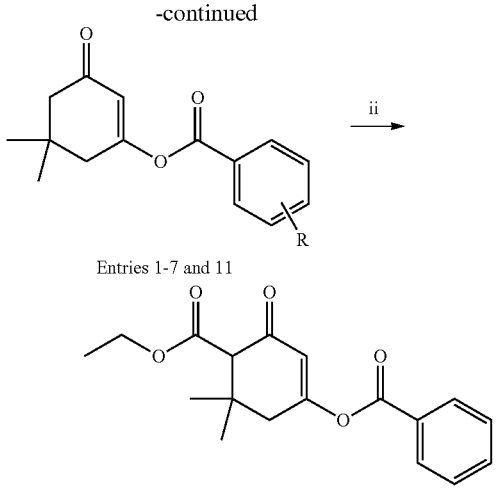

(i) pyridine, DCE, rt; (ii) ethyl cyanoformate, DMPU, LHMDS, THF, -78° C., 1 h.

Encouraged by the screening results that electron-donating group on the aryl ring plays beneficial role in TNF-α reduction and the assumption that amide would be more stable in vivo, we synthesized three enamides (entries 14-16) utilizing Buchwald's copper-mediated coupling between vinyl iodide and commercially available benzamides. Treatment of commercially available 5,5-dimethyl-cyclohexane-1, 3-dione with triphenylphosphine, iodine, and triethylamine in acetonitrile efficiently afforded vinyl iodide, which subsequently participated in a copper-mediated cross-coupling reaction. Thus, vinyl iodide and the benzamides were successfully coupled in the presence of substoiciometric amounts of Cur, N, N-dimethylglycine, and $Cs_2CO_3$ to produce three enamides (entries 14-16) respectfully, as follows:

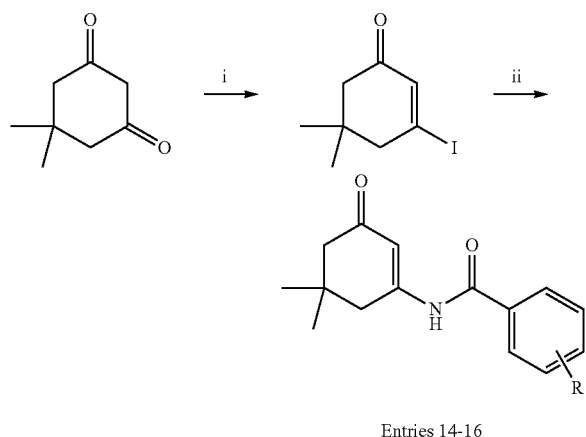

Entries 14-16
(i) $PPh_3$, $I_2$, $NEt_3$, $CH_3CN$, rt, 3 d. (ii) benzamide, CuI, N,N-dimethylglycine, $Cs_2CO_3$, dioxane, 60° C., 12 h.

The compounds of the present invention can be prepared and administered in a wide variety of oral and parenteral dosage forms. Thus, the compounds of the present invention can be administered by injection, that is, intravenously, intramuscularly, intracutaneously, subcutaneously, intraduodenally, or intraperitoneally. Also, the compounds of the present invention can be administered by inhalation, for example, intranasally. Additionally, the compounds of the present invention can be administered transdermally. It will be obvious to those skilled in the art that the following dosage forms may comprise as the active component, either compounds or a corresponding pharmaceutically acceptable salt of a compound of the present invention.

For preparing pharmaceutical compositions from the compounds of the present invention, pharmaceutically acceptable carriers can be either solid or liquid. Solid form preparations include powders, tablets, pills, capsules, cachets, suppositories, and dispersible granules. A solid carrier can be one or more substances which may also act as diluents, flavoring agents, solubilizers, lubricants, suspending agents, binders, preservatives, tablet disintegrating agents, or an encapsulating material.

In powders, the carrier is a finely divided solid which is in a mixture with the finely divided active component.

In tablets, the active component is mixed with the carrier having the necessary binding properties in suitable proportions and compacted in the shape and size desired.

The powders and tablets preferably contain from two or ten to about seventy percent of the active compound. Suitable carriers are magnesium carbonate, magnesium stearate, talc, sugar, lactose, pectin, dextrin, starch, gelatin, tragacanth, methycellulose, sodium carboxymethylcellulose, a low melting wax, cocoa butter, and the like. The term "preparation" is intended to include the formulation of the active compound with encapsulating material as a carrier providing a capsule in which the active component, with or without other carriers, is surrounded by a carrier, which is thus in association with it. Similarly, cachets and lozenges are included. Tablets, powders, capsules, pills, cachets, and lozenges can be used as solid dosage forms suitable for oral administration.

For preparing suppositories, a low melting wax, such as a mixture of fatty acid gycerides or cocoa butter, is first melted and the active component is dispersed homogeneously therein, as by stirring. The molten, homogeneous mixture is then poured into convenient sized molds, allowed to cool, and thereby to solidify.

Liquid form preparations include solutions, suspensions, mouth rinses, retention enemas, and emulsions, for example water or water propylene glycol solutions. For parenteral injection, liquid preparations can be formulated in solution in aqueous polyethylene glycol solution.

Aqueous solutions suitable for oral use, such as mouth rinses, can be prepared by dissolving the active component in water and adding suitable colorants, flavors, stabilizing, and thickening agents as desired.

Aqueous suspensions suitable for oral use, such as toothpastes, can be made by dispersing the finely divided active component in water with viscous material, such as natural or synthetic gums, resins, methylcellulose, sodium carboxymethylcellulose, and other well-known suspending agents.

Also included are solid form preparations which are intended to be converted, shortly before use, to liquid form preparations for oral administration. Such liquid forms include solutions, suspensions, and emulsions. These parparations may contain, in addition to the active component, colorants, flavors, stablizers, buffers, artificial and natural sweetners, dispersants, thickeners, solubilizing agents, and the like.

The pharmaceutical preparation is preferably in unit dosage form. In such form, the preparation is subdivided into unit doses containing appropriate quantities of the active component. The unit dosage form can be a packaged preparation, the package containing discrete quantities of the preparation, such as packeted tablets, capsules, and powders in vials or ampoules. Also, the unit dosage form can be a capsule, tablet; cachet, or lozenge itself, or it can be the appropriate number of any of these in packaged form.

The quantity of active component in a unit dose preparation may be varied or adjusted from 0.5 mg to 100 mg, preferably 2.5 to 80 mg according to the particular application and the potency of the active component. The composition can, if desired, also contain other compatible therapeutic agents.

To assist in understanding the present invention, the following Examples are included. The experiments relating to this invention should not, of course, be construed as specifically limiting the invention and such variations of the invention, now known or later developed, which would be within the purview of one skilled in the art are considered to fall within the scope of the invention as described herein and hereafter claimed.

Example 1

Periodontal Disease

In one embodiment of the invention, as an example, Kava-241 was shown to reduce inflammation in induced periodontitis. The effect of Kava-241 on periodontal destruction in a collagen antibody primed oral gavage model of periodontitis was evaluated. In this example, experimental periodontitis was induced by oral gavage of *P. gingivalis*+ type II collagen antibody (AB) in mice during 15 days. Mice were treated with Kava-241 concomitantly or prior to *P. gingivalis* gavage and compared to untreated mice. Comprehensive histomorphometric analyses were performed. Oral gavage with *P. gingivalis* resulted in induced mild epithelial down-growth and alveolar bone loss, while oral gavage with additional AB priming had greater tissue destruction in comparison with gavage alone (p<0.05). Kava-241 treated significantly (p<0.05) reduced epithelial down-growth (72%) and alveolar bone loss (36%) in the *P. gingivalis*+AG group. The Kava-241 effect was associated with a reduction in inflammatory cell counts within soft tissues and an increase in fibroblasts. Accordingly, Kava-241 demonstrated the effect of being useful in the prevention and treatment of inflammation and alveolar bone loss associated with periodontitis.

Example 2

Rheumatoid Arthritis and Reduction of TNF-α Secretion

Kava-241 (I-BC-241) is a compound derived from kavain and has been synthesized as described previously. In this example, we evaluated the systemic and articular effects of Kava-241 in an infective arthritis murine model triggered by *P. gingivalis* bacterial inoculation and primed with collagen antibody cocktail (CIA) to induce joint inflammation and tissular destruction. Arthritis was induced in twenty-eight six-week-old, pathogen-free DBA1/BO male mice by two consecutive injections of ArthritoMab (AB) Antibody cocktail (CIA-MAB-2C, MD Bioproducts, Oakdale, Minn., USA), the first injection of 7 mg at baseline, followed by a second injection of 4 mg at day 5. For *P. gingivalis* injected groups, 3 intraperitoneal injections of $5.10^8$ bacteria/100 µl were performed at days 2, 8 and 11. Mice were sacrificed after 17 days. Clinical inflammation score and radiological analysis of the paws were performed continuously while histological assessment was obtained at sacrifice. Forepaws were evaluated to score arthritis using a visual qualitative assessment scoring as follow: 0) no paw swelling, 1) mild swelling, 2) moderate swelling, 3) severe swelling (22). Inflammation was also evaluated with X-rays examination. Mice exposed to *P. gingivalis*, CIA cocktail and treated concomitantly with Kava-241 exhibited reduced clinical inflammatory score and decreased number of inflammatory cells and osteoclasts within joint. Kava-241 treatment also decreased significantly TNF-α in serum from mice injected with a TLR 2/4 ligand, *P. gingivalis*.-lipopolysaccharide (LPS). Finally, bone-marrow derived macrophages infected with *P. gingivalis* and exposed to Kava-241 displayed reduced TLR-2/4, reduced MAPKs related signal elements and reduced LITAF all explaining the observed reduction of TNF-α secretion. These results, taken together, exemplify the novel properties of Kava-241 in the management of inflammatory conditions especially TNF-α related diseases such as infective rheumatoid arthritis RA.

Example 3

Kavain Analog Screening

To identify compounds with strong anti-inflammatory properties, kavain analogs were tested in a screening assay based on TNF-□ inhibition in BMM infected with *P. gingivalis* (FIG. 1B). This screen identified Kava-205Cl (5,5-dimethyl-3-oxocyclohex-1-en-1-yl 4-chlorobenzoate) and its methylated analog Kava-205Me (5,5-dimethyl-3-oxocyclohex-1-en-1-yl 4-methylbenzoate) (FIG. 1B) as effective inhibitors of TNF-□ secretion (z=−0.99 and z=−1.07 respectively). In THP-1 and BMM infected with *P. gingivalis*, a dose-response evaluation was performed and showed that treatment with Kava-205Me reduced significantly TNF-□ secretion even at the lowest tested dose (10 □g/ml) (FIG. 2A, B) emphasizing the anti-inflammatory effect of tested compound in both murine and human cells.

Example 4

Kava-205 Significantly Reduced *P. gingivalis*-Induced Cytokine Secretion from Macrophages

*P. gingivalis* is able to induce sustained recruitment of immune cells such as neutrophils and T-lymphocytes, whose presence is associated with excessive inflammation and tissue destruction at infectious sites. To evaluate the effect of Kava-205Me on the secretion of chemokines and cytokines from BMM exposed to *P. gingivalis*, a multiplex analysis was performed that compared *P. gingivalis* infected cells with and without treatment with Kava-205Me. As expected, *P. gingivalis* infection significantly increased secretion of IL-12, IFN-γ, MIP-1β, RANTES, IL-10, G-CSF and eotaxin. Treatment with Kava-205Me significantly reduced the concentrations of such chemokines and cytokines (FIG. 3). Moreover, the gene expression of ACP5, an osteoclast specific gene, was evaluated in BMM infected with *P. gingivalis* with or without Kava-205Me treatment. As observed for inflammatory cytokines, *P. gingivalis* increased significantly ACP5 gene expression and Kava-205Me treatment reduced its expression illustrating a potential protective effect on bone (FIG. 2C).

Example 5

Kavain-205Me Reduced *P. gingivalis*-Induced Calvarial Destruction

In an acute model of *P. gingivalis* infection, Kava-205Me was administered to evaluate its anti-inflammatory and pro-healing properties in vivo. In this calvarial model, injection of *P. gingivalis* induced formation of a cutaneous abscess characterized by dermal inflammation and bone destruction (FIG. 4). Administration of Kava-205Me significantly increased the rate of healing (FIG. 4B). At the histological level, treatment with Kava-205Me reduced significantly soft tissue inflammation (FIG. 4C, D). Moreover, a trend of reduction in osteoclastic activity was also observed after treatment (FIG. 4D).

Example 6

Systemic Administration of Kava-205Me Significantly Reduced Infective Arthritis-Associated Joint Destruction To evaluate the systemic effect of Kava-205Me, an infective arthritis was induced in mice by the combined insults of *P. gingivalis* and AB peritoneal injection. After 10 days, significant paw swelling was observed, confirming the establishment of joint inflammation and a destructive process (FIG. 5). Interestingly, systemic administration of Kava-205Me significantly decreased *P. gingivalis*-induced paw swelling at the 32 day time point (FIG. 5A, B). This anti-inflammatory effect was confirmed histologically (FIG. 5C). A significant reduction of the inflammatory infiltrate in paw tissue sections was observed in animals exposed to *P. gingivalis* and treated by Kava-205Me. In contrast, untreated *P. gingivalis* exposed animals. exhibited a significant inflammatory infiltrate dominated by neutrophils and lymphocytes at the same timepoint (FIG. 5C). Congruent with these results, Kava-205Me treatment of *P. gingivalis*-exposed animals was also found to reduce the osteoclastic activity of the infiltrate, as evidenced by a reduction in the number of TRAP positive multinucleated cells in contact with bone. In contrast, *P. gingivalis*-exposed animals left untreated exhibited a significant increase of the number of TRAP positive multinucleated cells in contact with bone (FIGS. 5C, D).

The preceding preferred embodiments are illustrative of the practice of the invention. It is to be understood, however, that other expedients known to those of skill in the art, or disclosed herein, may be employed without departing from the spirit of the invention or the scope of the claims.

What is claimed:

1. An active pharmaceutical compound for treating inflammation wherein said compound is
   5,5-dimethyl-3-oxocyclohex-1-en-1-yl 3,4-difluorobenzoate,
   4-(ethoxycarbonyl)-5,5-dimethyl-3-oxocyclohex-1-en-1-yl 4-methoxybenzoate,
   4-(ethoxycarbonyl)-5,5-dimethyl-3-oxocyclohex-1-en-1-yl benzoate,
   4-(ethoxycarbonyl)-5,5-dimethyl-3-oxocyclohex-1-en-1-yl 3,4-difluorobenzoate,
   5,5-dimethyl-3-oxocyclohex-1-en-1-yl 3,4-dimethoxybenzoate,
   4-(ethoxycarbonyl)-5,5-dimethyl-3-oxocyclohex-1-en-1-yl 4-(benzyloxy)benzoate,
   4-(ethoxycarbonyl)-5,5-dimethyl-3-oxocyclohex-1-en-1-yl 4-ethoxybenzoate,
   or a pharmaceutically acceptable salt thereof.

2. A pharmaceutical composition, formulated for treating inflammation by inhibiting cytokine TNF-a, comprising
   5,5-dimethyl-3-oxocyclohex-1-en-1-yl 3,4-difluorobenzoate,
   4-(ethoxycarbonyl)-5,5-dimethyl-3-oxocyclohex-1-en-1-yl 4-methoxybenzoate,
   4-(ethoxycarbonyl)-5,5-dimethyl-3-oxocyclohex-1-en-1-yl benzoate,
   4-(ethoxycarbonyl)-5,5-dimethyl-3-oxocyclohex-1-en-1-yl 3,4-difluorobenzoate,
   5,5-dimethyl-3-oxocyclohex-1-en-1-yl 3,4-dimethoxybenzoate,
   4-(ethoxycarbonyl)-5,5-dimethyl-3-oxocyclohex-1-en-1-yl 4-(benzyloxy)benzoate, or
   4-(ethoxycarbonyl)-5,5-dimethyl-3-oxocyclohex-1-en-1-yl 4-ethoxybenzoate,
   or a pharmaceutically acceptable salt thereof and more than one pharmaceutically acceptable carrier.

* * * * *